United States Patent [19]

Bray Jr.

[11] Patent Number: 5,681,337
[45] Date of Patent: Oct. 28, 1997

[54] BONE SHAVER

[76] Inventor: Robert S. Bray Jr., 28660 Wagon Rd., Agoura, Calif. 91305

[21] Appl. No.: 485,098

[22] Filed: Jun. 7, 1995

[51] Int. Cl.[6] .................................................. A61B 17/32
[52] U.S. Cl. .................................................. 606/170; 606/83
[58] Field of Search ........................... 606/79, 83, 170, 606/171, 172

[56] References Cited

U.S. PATENT DOCUMENTS

| 4,574,803 | 3/1986 | Storz | 606/171 |
|---|---|---|---|
| 4,733,663 | 3/1988 | Farley | 606/171 |
| 5,273,519 | 12/1993 | Koros et al. | 606/171 |
| 5,385,570 | 1/1995 | Chin et al. | 606/170 |
| 5,451,227 | 9/1995 | Michaelson | 606/83 |

FOREIGN PATENT DOCUMENTS

| 614647-A2 | 9/1994 | European Pat. Off. | 606/83 |
|---|---|---|---|
| 93/04635 | 3/1993 | WIPO | 606/171 |

OTHER PUBLICATIONS

The Surgical Armamentarium by American V. Mueller p. 1080, 1980.

*Primary Examiner*—Michael Buiz
*Assistant Examiner*—Patrick W. Rasche
*Attorney, Agent, or Firm*—Christie, Parker & Hale, LLP

[57] ABSTRACT

A bone shaver comprises a top plate with a fixed handle fixedly attached to the top plate and a bottom plate slidably attached to the top plate. The top plate further comprises an anvil at its end. The bottom plate comprises a foot plate and a cutting edge on the foot plate. A movable handle is attached to the bottom plate. Movement of the movable handle towards the fixed handle results in movement of the bottom plate towards the top plate. A cutting edge is provided on the foot plate to thereby cut tissue when the handles are squeezed together.

12 Claims, 5 Drawing Sheets

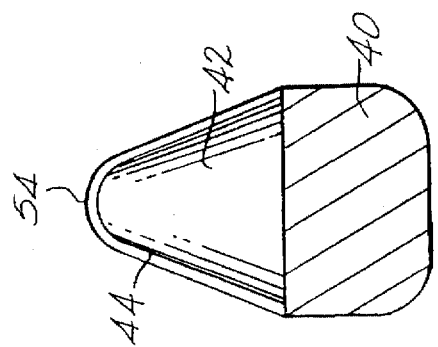
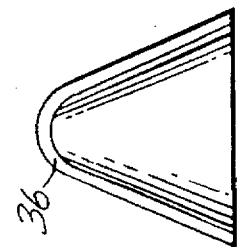
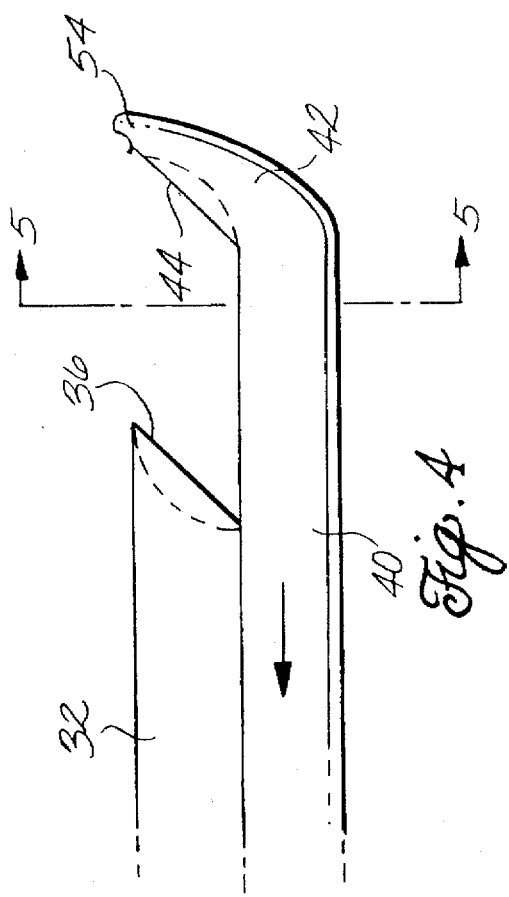
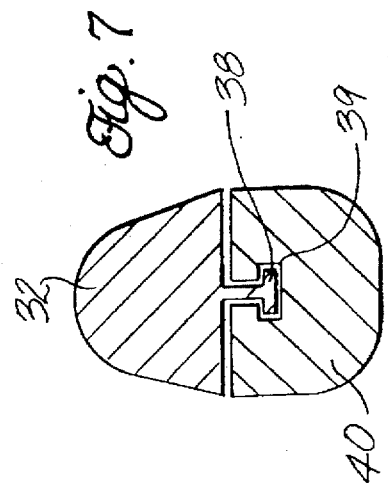

BONE SHAVER

FIELD OF THE INVENTION

The present invention relates to surgical instruments useful for shaving bone, especially during spinal surgery. More specifically, the present invention is directed to a Rongeur type instrument useful for removing bone from vertebral laminae as well as bone in other locations.

BACKGROUND OF THE INVENTION

A laminectomy punch, also known as a Kerrison's punch or a Colclough Rongeur, is an instrument used during spinal surgery procedures especially laminectomies and interlaminar laminotomies. These spinal surgical procedures decompress nerve tissue affected by spinal cord tumors, spinal canal stenosis, or due to various other causes.

A laminectomy is a surgical procedure where the posterior arch or lamina of a vertebra is excised. In a laminectomy procedure, the laminectomy punch is used to gradually remove the vertebral lamina to open a lateral recess of the spinal canal while preserving intervertebral joints.

An interlaminar laminotomy is a division of the lamina of a vertebra. In an interlaminar laminotomy, the laminectomy punch is used to prepare the surgical field for the removal of compressive factors such as a thickened ligamentum flavum, hypertrophic bulging of the superior articular process, or a herniated intervertebral disc.

In both procedures, the laminectomy punch is first used as a probe. The laminectomy punch probes the areas to be isolated and cleaned. After the probing, the laminectomy punch is used to remove the lamina, ligamentum flavum, or other tissues to provide a working surface at the surgical site. The laminectomy punch is also useful in other surgical procedures such as to cut away the skull in brain surgeries and to remove bone in the nose and face during facial surgeries.

A conventional laminectomy punch 10 is shown in FIGS. 1a–1d. When the laminectomy punch is used to cut tissue and bone the handles 12 are squeezed together by the surgeon's hand. Force is applied to the top plate 14 and the cutting edge 16 to move the top plate towards the foot plate 18 and anvil 19 until the cutting edge fits tightly against the anvil. (The arrow in FIG. 1b indicates the direction of the force applied to the top plate and the direction of the movement of the top plate relative to the stationary bottom plate). The top plate and bottom plate are slidably attached to each other with a conventional tongue and grove mount (not shown). Tissue or bone trapped between the top plate and foot plate is cut by the cutting edge as it moves toward the anvil. As illustrated in FIG. 1b, the foot plate and distal end of the top plate are hollowed out in order to contain the cut tissue or bone. Additionally, the cutting edge (FIG. 1d) and the foot plate (FIG. 1c) are both D shaped.

FIG. 2 illustrates a cross section of a thoracic vertebra just caudal to the vertebral pedicles. The spinal cord 102 is centrally located in the spinal canal which is the canal formed within the vertebra. The vertebral body 104, laminae 116, and pedicles (not shown) make up the boundaries of the spinal canal. The spinal cord is surrounded by pia mater 110, dura mater 106, and epidural fat 112. Also illustrated in FIG. 2 is the spinous process 114 and the delicate nervous tissues of the nerve root 108 (and its two components: the dorsal root 118 and the ventral root 122) and the spinal ganglion 120.

The surgical use of the conventional laminectomy punch presents a number of problems and requires a great deal of care to prevent damage to the spinal cord and nerve roots. In order for a surgeon to perform a laminectomy procedure and cut the bone of the vertebral lamina with a laminectomy punch, the surgeon anchors the foot plate of the laminectomy punch inside the spinal canal juxtaposed to the vertebral lamina. The surgeon uses the distal side of the foot plate to push the fat and nervous tissue away from the bone to be cut. The surgeon then, using the fingers and palm of the surgeon's hand, squeezes the handles of the laminectomy punch together. While squeezing the handles, the surgeon applies force to the cutting edge of the top plate with the surgeon's palm in a direction towards the foot plate (see the arrow in FIG. 1b indicating the direction of the force applied to the top plate). The force applied is needed to cut through the hard bone of the lamina. Unfortunately, the force applied is also in the direction of the delicate nervous tissue of the spinal cord and nerve roots. This presents a problem in that once the bone is completely cut the laminectomy punch tends to jerk away from the surgeon and towards the patient's delicate nervous tissue. Thus, a sudden small jerk of the laminectomy punch towards the spinal cord can cause serious damage to the patient's spinal cord and nerves.

There are many other problems with the current laminectomy punch. Because the cutting edge to move in a direction toward the nerves and spinal cord, the possibility of pinching or otherwise damaging nerves at the site of the surgery increases. This is particularly important in cervical surgeries where the vertebrae are relatively small and the nerves are more susceptible to damage. Also the movement of the top plate towards the bottom plate is controlled by the surgeon's palm of his or her hand. Unfortunately, the fine motor control of the hand is in the fingers, not in the palm.

Another problem with the current laminectomy punch is that it is designed for use in cutting completely through the vertebral lamina. Many times hypertrophic bone growth occurs on the spinal canal side of the lamina and causes pressure on the spinal cord or other nervous tissue. The current laminectomy punch cannot be used to shave off the hypertrophic bone growth to widen the spinal canal while leaving the lamina intact.

A further problem with the conventional laminectomy punch is that the force applied to the cutting edge is transferred to the foot plate. Because of this force, the foot plate has a tendency to break off. To prevent breakage, the foot plate must be made thick enough to withstand the forces placed on it. Unfortunately, the thickness of the foot plate inhibits or hinders the probe function of the laminectomy punch.

An additional problem occurs because of the D shape of the cutting edge and anvil (see FIGS. 1c and 1d). The D shape dictates that the surgeon removes tissue or bone the width of the cutting edge and anvil. In the cervical area, where the vertebra are relatively small and close together, the surgeon has to start a procedure with a very small sized laminectomy punch. As the procedure progresses, the surgeon incrementally replaces the laminectomy punch with larger punches until the procedure is completed. Thus, many laminectomy punches of differing sizes have to be sterilized and prepared for any given surgery.

Accordingly, there is a need for a bone shaving device which reduces the possibility of damage to nerves during use. It is desirable that the thickness of the foot plate of the bone shaving device be reduced to enhance the use of the device as a probe and not to damage already compressed structures because of the thickness of the foot plate. Additionally, it is desirable to have a bone shaving device with a tapered cutting edge that gives the surgeon a range of widths of tissue or bone to remove with the use of only one device. It would also be advantageous to have the movement of the bone shaving device controlled by the fine motor control of the surgeon's fingers.

SUMMARY OF THE INVENTION

The present invention overcomes the above problems and relates to a bone shaver comprising a top plate with a fixed handle fixedly attached to the top plate and a bottom plate slidably attached to the top plate. The bottom plate comprises a foot plate with a cutting edge provided on the foot plate. A moveable handle is attached to the bottom plate to thereby move the cutting edge toward the top plate.

The bone shaver according to the present invention is designed to perform all the functions of the conventional laminectomy punch and is also designed to be useful in shaving off hypertrophic bone growth while maintaining the integrity of the vertebral lamina. For bone shaving, the surgeon introduces the cutting edge of the foot plate behind the hypertrophic growth on the inside of the lamina. The surgeon then squeezes the handles together to bring the cutting edge across the inside surface of the lamina shaving off the hypertrophic bone. The lamina itself is preserved and is not cut completely through.

In a preferred embodiment, the cutting edge is tapered such that it can be introduced into a relatively small area to begin shaving off a small amount of tissue or bone. As the bone shaver is used, a wider area of bone is shaved off as the bone shaver is gradually introduced further into the surgical site.

The bone shaver according to the present invention is replete with advantages. The movement of the cutting edge is away from the spinal cord and nerve roots. When the bone shaver is used in spinal surgeries the force applied to the cutting edge is directed away from the delicate nervous tissue of the spinal cord and nerve roots thereby preventing injury to these structures. The bone shaver can also shave off unwanted bone without destroying the integrity of the vertebral lamina. Because the cutting edge is located on the foot plate, the thickness of the foot plate is not as critical as the thickness of the conventional laminectomy punch. Thus, the thickness at the base of the foot plate can be left the same to prevent breakage and the thickness at the tip of the foot plate can be reduced to enhance the probing function of the bone shaver and to allow easier access in already compressed structures. Additionally, if the cutting edge is tapered the bone shaver can perform the function of many different sized conventional laminectomy punches. Another advantage is that the movement of the cutting edge and bottom plate are controlled by the surgeon's finger tips, which increases the safety of the surgical procedures and the ease of use of the shaver.

As will be realized, the invention is capable of other and different embodiments and its several details are capable of modification in various respects, all without departing from the spirit and scope of the present invention. Accordingly, the drawings and detailed description are to be regarded as illustrative in nature and not as restrictive.

BRIEF DESCRIPTION OF THE DRAWINGS

Features, aspects and advantages of the invention will be more fully understood when considered with respect to the following detailed description, appended claims and accompanying drawings where:

FIG. 4 is an enlarged side prospective view of the distal end of the bone shaver of the present invention;

FIG. 5 is a prospective view partially in cross section of the cutting edge on the foot plate of the present invention taken along the line 5—5 of FIG. 4;

FIG. 6 is an end prospective view of the anvil of the top plate of the bone shaver of the present invention; and FIG. 7 is a cross section of the bone shaver illustrated in FIG. 3 taken along the line 7—7.

DETAILED DESCRIPTION

The present invention is directed to a bone shaver for use in spinal surgery. The bone shaver of the present invention has the advantage of allowing the surgeon to control the movement of the cutting edge of the shaver in a direction away from the nerves at the site of the surgery when the shaver is in use. The design also greatly reduces the mass of the tip of the foot plate, thus enhancing the probe function of the bone shaver.

Figure 1A:
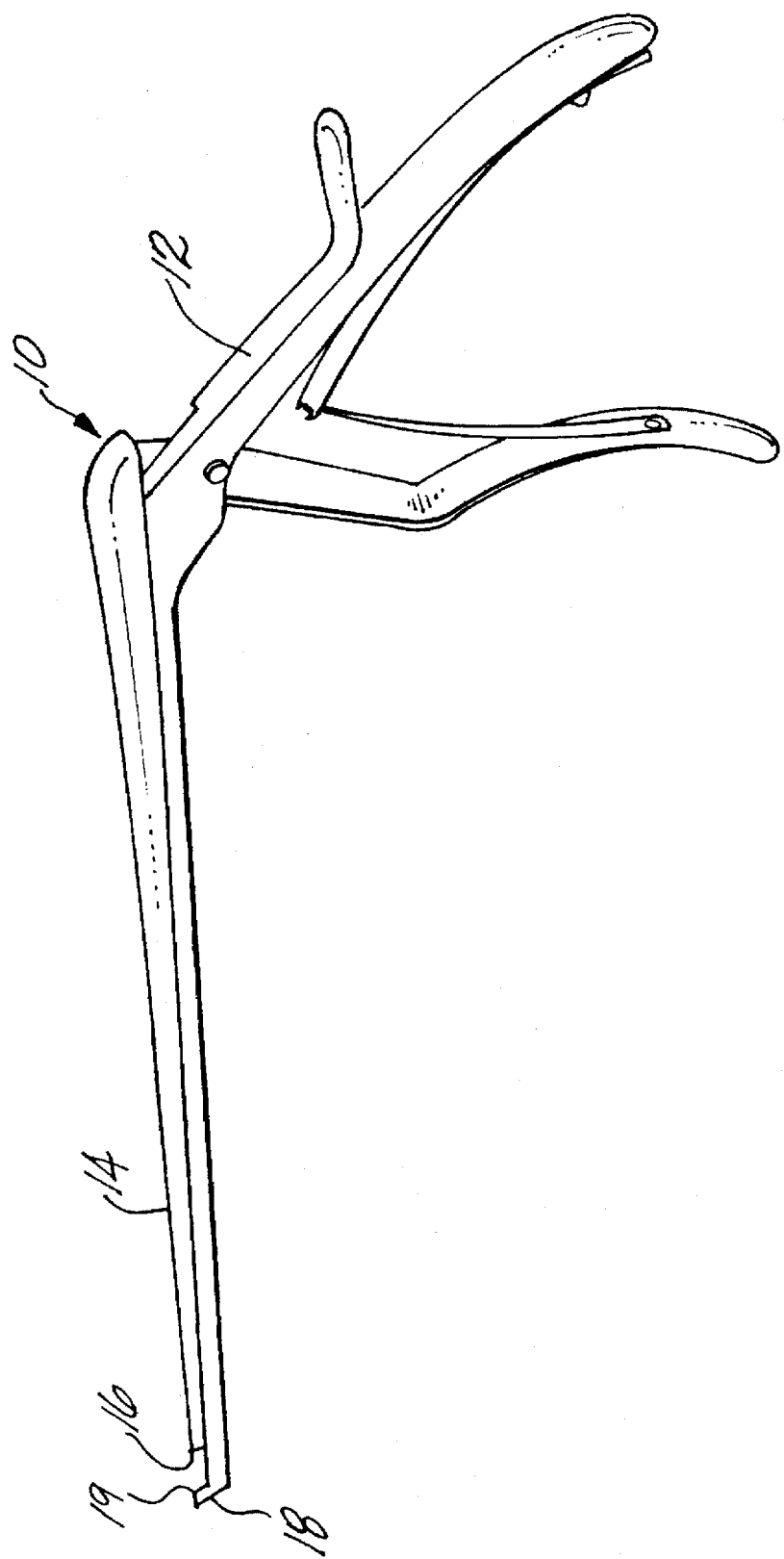
FIG. 1a is a side perspective view of a conventional laminectomy punch.
Figure 1B:
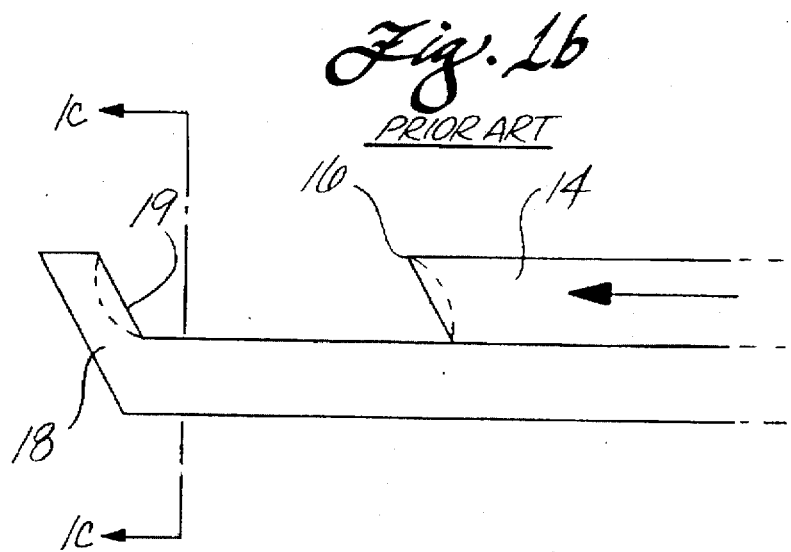
FIG. 1b is an enlarged side perspective view of the distal end of the conventional laminectomy punch.
Figure 1C:
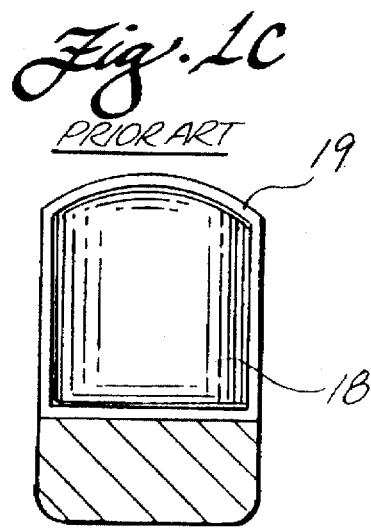
FIG. 1c is a perspective view partially in cross section of the anvil section of the foot plate of the conventional laminectomy punch taken along the line 1c—1c of FIG. 1b.
Figure 1D:
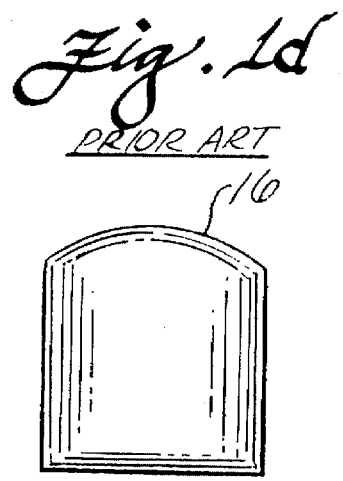
FIG. 1d is an end perspective view of the cutting edge of the top plate of the conventional laminectomy punch.
Figure 2:
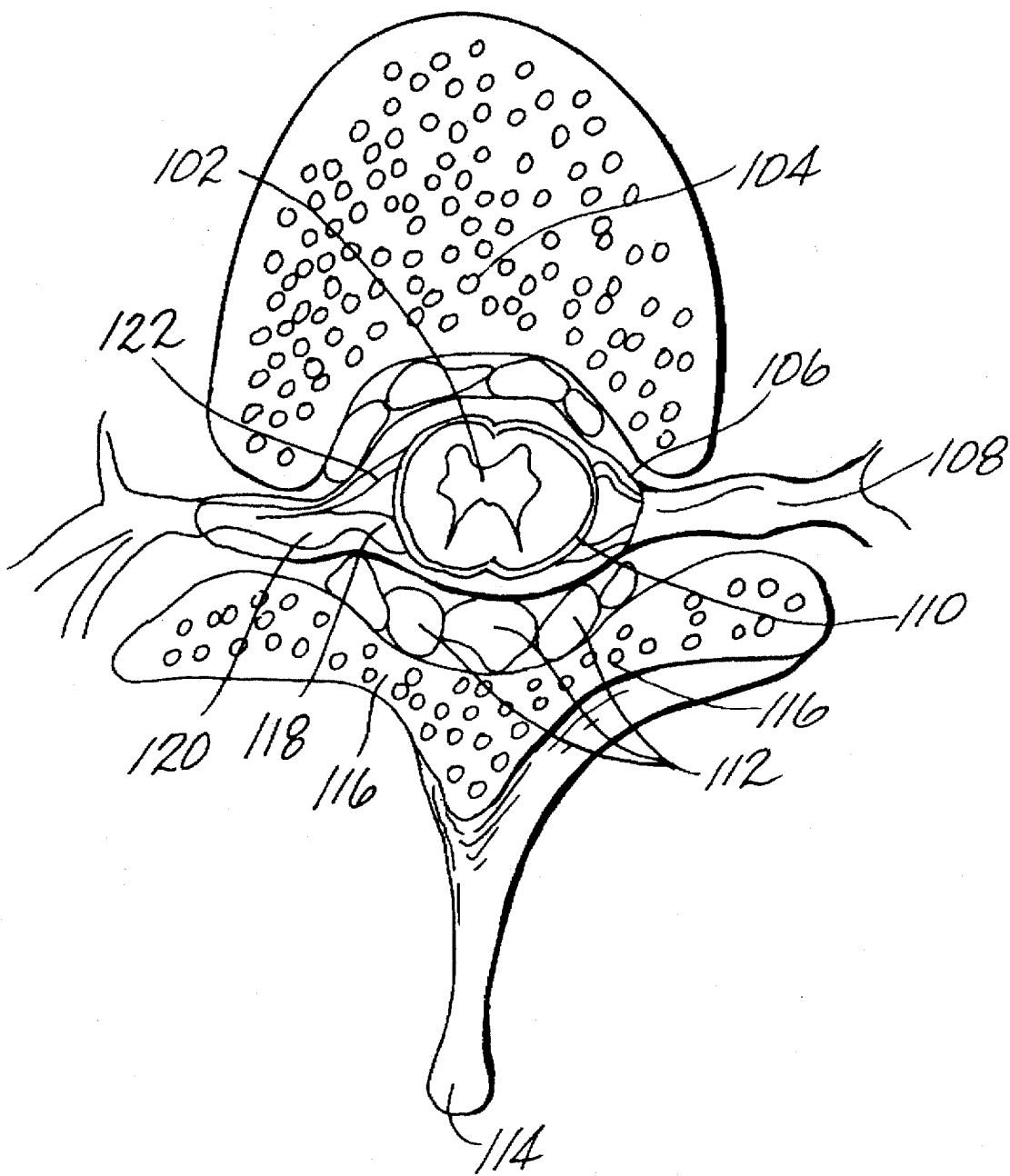
FIG. 2 is a cross section of a patient's spine through a thoracic vertebra.
Figure 3:
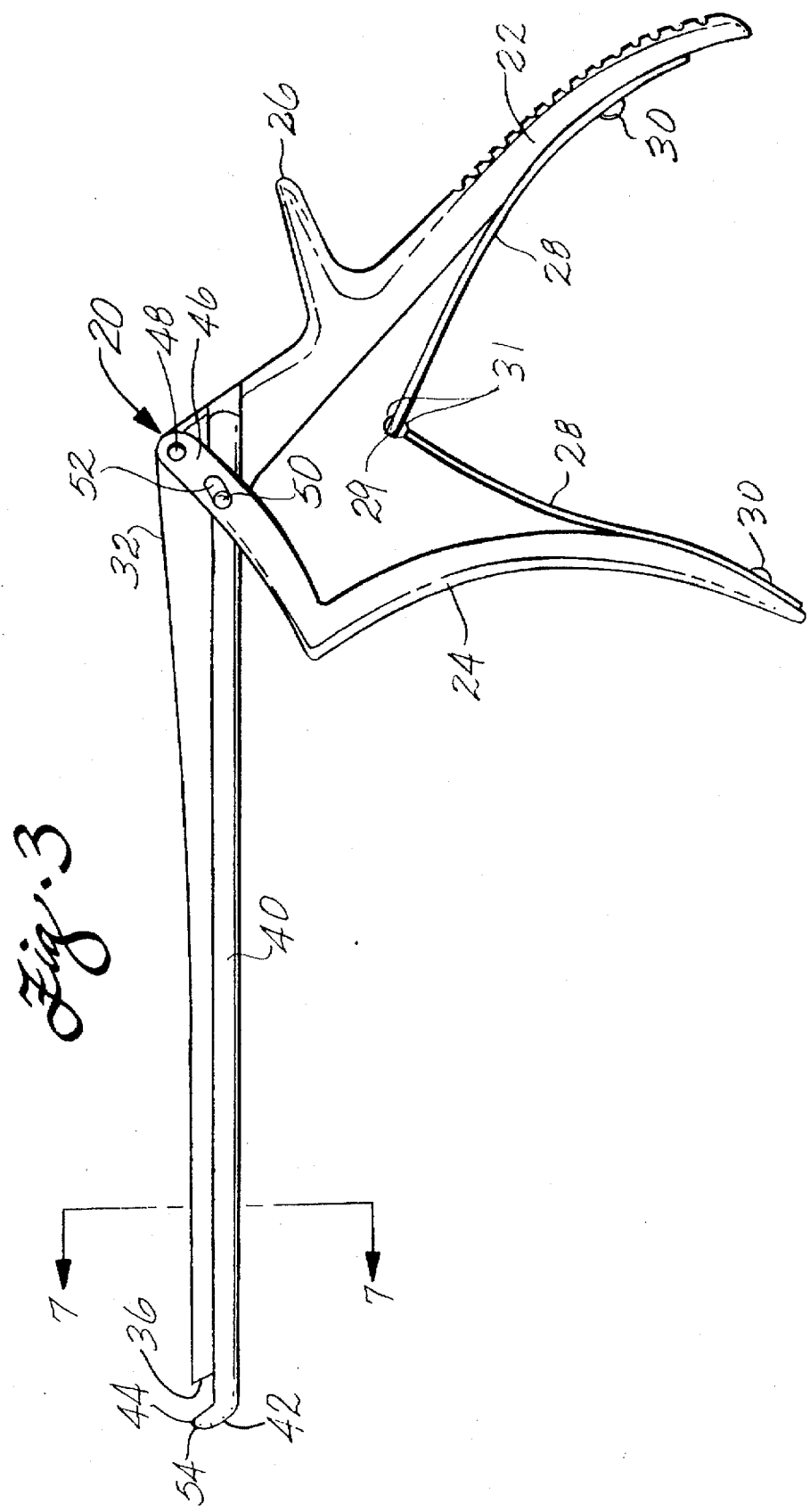
FIG. 3 is side perspective view of a bone shaver of the present invention.

The bone shaver of the present invention is illustrated in FIGS. 3-7. The bone shaver 20 comprises a stationary handle 22 pivotally attached to movable handle 24. The handles are curved members to accommodate the shape of a surgeon's hand. The fixed handle may include a projection 26 for bracing between the thumb and first finger of the user of the punch. The movable handle may be smooth or, as illustrated, may include an angled section for bracing between the first finger and the second finger of the user of the shaver.

Disposed between the fixed and movable handles are leaf springs 28, although other springs known in the art could be used. The leaf springs are pivotally joined to each of the handles by screws 30 and to each other by a ball 29 in one spring which fits into a socket 31 on the other spring. The springs deform when the handles are compressed and when the handles are released the leaf springs return the handles to their resting position.

The fixed handle 20 is fixedly attached to the proximal end of top plate 32. In the preferred embodiment, the fixed handle and the top plate are unitarily constructed out of the same piece of material. The top plate comprises an elongated, member having proximal and distal ends and a generally triangular cross-sectional shape. The top plate has a distal tip at its distal end having an anvil like structure 36.

The movable handle is attached to the bottom plate 40 such that when the handles are compressed, i.e., the moveable handle is moved back toward the fixed handle, the bottom plate is retracted or moved relative to the stationary top plate (the direction of the bottom plate's movement is indicated by the arrow in FIG. 4).

The bottom plate comprises an elongated member having proximal and distal ends and a generally rectangular cross-sectional shape. At the distal tip of the distal end of the bottom plate there is provided a foot plate 42 that has a cutting edge 44 on its proximally facing surface.

The bottom plate is connected at its proximal end to the movable handle by a connector 46 such that when the movable handle is compressed the bottom plate, foot plate, and cutting edge are moved proximally toward the fixed handle. In one embodiment of the present invention, the connector 46 is pivotally attached to the top plate by pin 48 to anchor the movable handle to the top plate. The bottom plate is pivotally attached to the movable handle by pivot pin 50 protruding from the side of the bottom plate and inserted within oblong aperture 52 of the moveable handle.

Towards the distal end of the top plate 32 is a tongue 38 that projects outward from the surface juxtaposed to the bottom plate. Towards the distal end of the bottom plate is a grove 39 in the surface juxtaposed to the top plate that slidably accommodates the tongue 38 of the top plate. Thus, the distal ends of the top plate and bottom plate are slidably attached to each other by the tongue 38 of the top plate slidably mounted within the groove 39 of the bottom plate (see FIG. 7). When the movable handle is moved toward the fixed handle, the bottom plate is retracted relative to the fixed top plate and the cutting edge 44 is moved toward the anvil 36. The tongue and grove mounting ensures that the distal ends of the top plate and bottom plate stay aligned.

As noted above, at the distal tip of the bottom plate foot plate 42 is provided. On the surface of the foot plate is the cutting edge 44. As illustrated in FIGS. 4 and 5, the sharp cutting edge 44 is located on the proximal surface of the foot plate and is slightly recessed from the perimeter of the outer surface of the foot plate. This configuration is desirable in that the distal surface of the back can be used to probe the surgical site without the risk that the sharp cutting edge will accidentally cut or damage tissue.

The tip 54 of the foot plate is tapered such that the foot plate is generally triangular in shape. As illustrated in FIG. 5, the foot plate 42 is thicker at its junction with the bottom plate 40 and is much thinner at the tip 54. The thinness of the tip 54 enhances the probing function of the shaver and allows the shaver to be placed in a surgical site more easily. The thickness at the bottom of the foot plate helps the bone shaver to withstand the forces needed to cut bone. The proximal surface of the bottom plate is also slightly hollowed out as illustrated in FIG. 4 to allow for some or the cut bone to be captured within the hollow.

Located at the distal end of the top plate is the anvil like structure 36. The anvil like structure has a flat, relatively wide area that corresponds to the cutting edge 44 of the foot plate (see FIG. 6). The center of the anvil like structure optionally is hollowed out as illustrated, or can be completely flat (not shown). The anvil like structure is used to anchor the bone shaver around the tissue or bone to be cut. Tissue or bone trapped between the cutting edge of the bottom plate and the anvil like structure of the top plate will be shaved off as the cutting edge moves towards the anvil like structure. The anvil is also tapered to correspond to the taper of the foot plate.

In use, the surgeon first probes the surgical site with the distal surface of the foot plate. The surgeon then isolates bone or tissue to be shaved off with the bone shaver. The surgeon will then carefully place the bone shaver around the bone or tissue to be shaved off such that the tissue or bone is located between the cutting edge and the anvil like structure. The surgeon will then squeeze the handles together using his or her finger tips to control the motion of the foot plate and cutting edge. The tissue or bone is then shaved off by the cutting edge as it moves back towards the anvil like structure.

Use of the bone shaver of the present invention in a laminectomy procedure illustrates some of its advantages. After the patient's spine is identified and accessed by the surgeon, the foot plate of the bone shaver is introduced into the spinal canal under a vertebral lamina. The distal surface of the foot plate is used to probe the surgical site and to gently push nervous and other extra tissue away from any tissue to be cut. The surgeon then places the bone shaver around the lamina such that some of the lamina is located between the cutting edge of the foot plate and the anvil like structure of the top plate. The surgeon then squeezes the handles together using his or her finger tips to thereby move the cutting edge of the foot plate gently towards the anvil like structure of the top plate. The cutting edge is thus moving away from the delicate spinal cord and nervous tissue. If needed, the surgeon can apply extra force to the cutting surface by pulling the bone shaver away from the patient while squeezing the handles together. Because the cutting edge is moving away from the spinal cord and delicate nervous tissue, the safety factor is increased. If the bone shaver suddenly jerks during use, the bone shaver will be jerking away from all of the delicate structures of the patient.

The tip of the bone shaver is tapered such that only a small amount of bone can be removed during the surgeon's first use of the shaver at the surgical site. The size of the tip can vary from about 0.1 mm to about 3 mm. In a presently preferred embodiment, the tip is 0.5 mm wide. The surgeon then reinserts the bone shaver around the bone to gradually remove more bone. As the surgeon keeps repeating the process of cutting bone, the width of the bone removed is enlarged due to the tapering of the tip. The base of the bone shaver can vary from about 2 mm to about 10 mm. In a presently preferred embodiment, the base of the cutting edge is 3.0 mm wide. Thus, while using the preferred embodiment of the bone shaver the surgeon can start the surgical procedure with the tip of the bone shaver removing 0.5 mm of bone and end the procedure by removing 3.0 mm of bone using the base of the cutting edge.

The bone shaver of the present invention is preferably made of a material which is strong enough to withstand the forces to which it is subjected during use and which is sterilizable, preferably by autoclaving. One suitable material is stainless steel, although other materials are known in the art and would also be suitable.

The present invention is not to be limited to the specific designs shown which are merely illustrative. Various and numerous other arrangements may be devised by one skilled in the art without departing from the spirit and scope of this invention. The scope of the invention is defined in the following claims.

What is claimed is:

1. A bone shaver comprising:
   a top stationary plate having proximal and distal ends;
   a fixed handle immovably attached to the proximal end of the top plate;
   a movable bottom plate having proximal and distal ends slidably attached to the top plate wherein the distal end of the bottom plate is at a position distal to the distal end of the top plate and wherein the bottom plate comprises:
      a foot plate at the distal end of the bottom plate; and
      a cutting edge on the foot plate; and
   a movable handle attached to the proximal end of the bottom plate and movable with respect to the bottom plate whereby movement of the movable handle toward the fixed handle results in movement of the foot plate in a proximal direction toward the distal end of the top plate.

2. A bone shaver as recited in claim 1 wherein movement of the movable handle toward the fixed handle moves the cutting edge of the bottom plate toward the top plate.

3. A bone shaver as recited in claim 1 wherein the slidable attachment of the top plate to the bottom plate comprises:

a groove on the bottom plate; and a tongue on the top plate which fits into the groove on the bottom plate.

4. A bone shaver as recited in claim 1 wherein the distal end of the top plate comprises an anvil like structure.

5. A bone shaver as recited in claim 1 wherein the foot plate further comprises a tip and a base.

6. A bone shaver as recited in claim 1 wherein the foot plate further comprises a taper, the foot plate having a width at its tip of from about 0.1 mm to about 3 mm and a width at its base of from about 2 mm to about 10 mm.

7. A bone shaver as recited in claim 6 wherein the foot plate has a width at its tip of about 0.5 mm and a width at its base of about 3.0 mm.

8. A bone shaver as recited in claims 6 or 7 wherein the distal end of the top plate comprises an anvil like structure that is tapered to match the taper of the foot plate.

9. A bone shaver as recited in claim 6 wherein the foot plate comprises a recess.

10. A bone shaver as recited in claim 1 wherein the foot plate has a perimeter and the cutting edge is spaced apart from the perimeter.

11. A bone shaver comprising:

(a) a first handle;

(b) a first plate having proximal and distal ends immovably attached to the first handle;

(c) a second handle movably attached to the first handle;

(d) a second plate having proximal and distal ends attached to the second handle which is movable with respect to the second plate and slidably attached to the first plate whereby the distal end of the second plate is located at a position distal to the distal end of the first plate;

(e) a foot plate attached to the distal end of the second plate, said foot plate having a cutting edge facing the distal end of the first plate; and (f) whereby movement of at least one of the first and second handles toward the other of the first and second handles results in movement of the foot plate and cutting edge in a proximal direction toward the distal end of the first plate.

12. A bone shaver comprising:

a stationary plate having a distal end which forms a stop;

a movable plate movably connected to the stationary plate and extending beyond the distal end of the stationary plate, said movable plate having a cutting edge at its distal end facing the distal end of the stationary plate; and a stationary handle immovably attached to the stationary plate;

a movable handle attached to the movable plate and movable with respect to the stationary plate for moving the movable plate in a proximal direction relative to the stationary plate so that the cutting edge of the movable plate moves toward the distal end of the stationary plate.

\* \* \* \* \*